US010816457B2

(12) United States Patent
Caneda

(10) Patent No.: US 10,816,457 B2
(45) Date of Patent: Oct. 27, 2020

(54) SPECTROMETRIC PROBE FOR SAMPLING BULK MATERIAL AND AUTOMATIC SAMPLE TAKER FOR SAMPLING INCLUDING THE PROBE

(71) Applicants: TECNOCIENTIFICA, S.A., Manzanares El Read—Madrid, Espana (AR); ING. JORGENSEN & ASOC., Manzanares El Read—Madrid, Espana (AR)

(72) Inventor: Gustavo Daniel Caneda, Caba (AR)

(73) Assignees: TECNOCIENTIFICA, S.A., Buenos Aires (AR); ING. JORGENSEN & ASOC., Buenos Aires (AR)

(*) Notice: Subject to any disclaimer, the term of this patent is extended or adjusted under 35 U.S.C. 154(b) by 42 days.

(21) Appl. No.: 16/308,791

(22) PCT Filed: Jan. 22, 2018

(86) PCT No.: PCT/ES2018/070047
§ 371 (c)(1),
(2) Date: Dec. 10, 2018

(87) PCT Pub. No.: WO2018/146352
PCT Pub. Date: Aug. 16, 2018

(65) Prior Publication Data
US 2019/0187046 A1 Jun. 20, 2019

(30) Foreign Application Priority Data
Feb. 10, 2017 (AR) .............................. P20170100339

(51) Int. Cl.
*G01N 21/27* (2006.01)
*G01N 33/02* (2006.01)
(Continued)

(52) U.S. Cl.
CPC ......... *G01N 21/27* (2013.01); *G01N 21/3563* (2013.01); *G01N 21/8507* (2013.01);
(Continued)

(58) Field of Classification Search
CPC .. G01N 21/27; G01N 21/3563; G01N 21/359; G01N 21/8507; G01N 27/22; G01N 33/02
See application file for complete search history.

(56) References Cited

U.S. PATENT DOCUMENTS 3,789,671 A 2/1974 Larson
4,037,476 A 7/1977 MacCrabb
(Continued)

FOREIGN PATENT DOCUMENTS

DE 102004020350 A1 10/2005
WO WO2001069213 A2 9/2001
WO WO2009017721 A2 2/2009

*Primary Examiner* — Hina F Ayub
(74) *Attorney, Agent, or Firm* — Stites & Harbison PLLC; Sean P. Ritchie

(57) ABSTRACT

A spectrometric probe for sampling of bulk material and automatic sampler for sampling bulk material, which allows to obtain the composition parameters of the material to be sampled directly, avoiding the extraction and transfer of samples that shall be examined in external sections under the observation and analysis of trained and specialized personnel, thus optimizing operation times and reducing related costs.

7 Claims, 3 Drawing Sheets

(51) Int. Cl.
     *G01N 27/22*     (2006.01)
     *G01N 21/3563*     (2014.01)
     *G01N 21/85*     (2006.01)
     *G01N 21/359*     (2014.01)

(52) U.S. Cl.
     CPC .............. *G01N 27/22* (2013.01); *G01N 33/02* (2013.01); *G01N 21/359* (2013.01)

(56) References Cited

U.S. PATENT DOCUMENTS

| | | |
|---|---|---|
| 4,616,515 A | 10/1986 | Dancoine |
| 2007/0224853 A1 | 9/2007 | Mannhardt et al. |
| 2012/0086429 A1 | 4/2012 | Kluin et al. |
| 2012/0162650 A1* | 6/2012 | Wynn .................... G01N 21/01 356/432 |
| 2017/0370064 A1* | 12/2017 | Morgan .................. E02D 1/027 |

\* cited by examiner

SPECTROMETRIC PROBE FOR SAMPLING BULK MATERIAL AND AUTOMATIC SAMPLE TAKER FOR SAMPLING INCLUDING THE PROBE

RELATED APPLICATIONS

This application claims priority from International Patent Application No. PCT/ES2018/070047, filed Jan. 22, 2018, which claims priority from Argentina Application No. P 20170100339, filed Feb. 10, 2017, the entire disclosures of which are incorporated herein by this reference.

FIELD OF THE INVENTION

The present invention relates to the field of devices, means or arrangements used for the sampling of bulk material, such as post-harvest grains, and more particularly the invention relates to a spectrometric probe and an automatic sampler for directly sampling parameters of quality and composition of bulk materials in the same place in which they are stored, such as a silo, truck or transport wagon, without the need to take samples that has to be transferred to remote units for their examination and evaluation.

In the present description reference is made in an exemplary manner to the sampling of grains, this does not imply that the present invention is limited thereto, but that sampling can be carried out on different types of bulk materials, either independently or jointly with other devices, arrangements or related means for the sampling or treatment of such materials.

STATE OF THE ART PRIOR TO THE INVENTION

The sampling of post-harvest bulk material is well known, and it is known that it is a fundamental practice to know the conditions of, for example, grains, prior to their commercialization. In order to carry out the sampling, the methodology to be used will depend on the type of vehicle or means on which grains are transported to the silos or shipping ports. Among the methods, the following can be found: the sampling of grains supplied in sacks, probe sampling, sampling by emptying the sacks, sampling of grains supplied in bulk, sampling of the product in rest state, sampling of the product in movement, cone method, among so many others. In all cases, the moisture content measurement and the corresponding quality analyzes will be carried out on the final sample.

In relation to the sampling of grains in state of rest, generally grains are transported in trucks/wagons that get into verification plants so that sampling can be carried out by means of an automatic probe sampler. Taking into account that a manual sampling by an operator truck by truck would not only be inefficient and dangerous but also unfeasible, and that the truck queue would be interminable, an automatic sampler is used, which is a probe remotely commanded from a cabin, which is inserted several times and in different locations in the load of the truck, both in the chassis and in the trailer to carry out the sampling.

Once the probe is inserted between the grains stored in the chassis/trailer of the truck or wagon, a plurality of nozzles along the entire probe are automatically opened to allow the entry of the sample by gravity. Generally, samples are taken at the top, middle and bottom, the collected sample being sent to the receiver bed via a pneumatic arrangement well known in the art, which is separated by sections (Upper, Middle, Bottom and bottom nozzle). Thus, the trained operator performs a "commercial" visual quality control, which is a physical analysis in which the composition analysis of the samples is not performed. To carry out the composition analysis of grains, some samples shall be selected manually, making a set for their subsequent processing in a countertop spectrometer. From this last procedure, parameters of grains composition that were taken as samples are obtained, the results being compared with standard parameters to know if they are suitable for commercialization.

Although, the normal operation of a conventional automatic sampling takes an approximate time of between 2 to 3 minutes per truck/wagon, depending on the plant and operator, this lapse of time is much longer if it performs the composition analysis (protein, moisture, fat) of grains. This entails longer operation times, additional costs, and the need to strictly count on specialized personnel to carry out the analysis. In addition, the sample will not be 100 representative depending on the assembly of the set by the operator, generating subjectivity and handling costs.

By virtue of the foregoing, it would be advisable to have a new arrangement, device or sampler that allows the sampling of bulk material in order to directly know the composition parameters directly, without the need of taking samples that shall be transferred and incurring additional time or handling errors.

BRIEF DESCRIPTION OF THE INVENTION

It is therefore an object of the present invention to provide a spectrometric probe with a sampling module that is fitted or mounted on the probe in a manner that allows direct taking of the composition parameters of the bulk material, without the need to perform the sampling of the material.

It is yet another object of the present invention to provide a spectrometric probe that dramatically reduces operating times as well as related costs.

It is also another object of the present invention to provide a sampling module that operates directly with a spectrometer to carry out the composition analysis of the grains or bulk material.

It is still another object of the present invention to provide a spectrometric probe that performs non-invasive, non-destructive and innocuous sampling, which does not use reagents or generate chemical residues.

It is still another object of the present invention to provide simultaneous automatic operation, in real time, with a sampling process carried out on the bulk material.

It is still another object of the present invention to provide a sampling module that can operate in conjunction with a probe provided with a plurality of nozzles for taking samples or a probe without nozzles.

It is still another object of the present invention to provide a spectrometric probe for the sampling of bulk material that performs sampling directly, without the need of taking of samples which are then taken to outbuildings.

It is also another object of the present invention to provide a spectrometric probe for the sampling of bulk material comprising at least one sampling module mounted on a section of the probe and which is formed by a casing having at least one front wall that has a transparent inspection window, said casing also having a capacitive sensor that protrudes outside the casing to contact the mass of the bulk material to be sampled, and at least one optical sampling sensor being arranged inside said casing and directed according to a reading path towards said inspection window, the optical sampling sensor being operatively connected to a remote control panel.

It is still another object of the present invention to provide an automatic sampler for the sampling of bulk material fitted with the spectrometric probe, which comprises said probe driven by an articulated arm which has a plurality of nozzles located in at least one upper, intermediate and lower section of the probe for taking samples, the articulated arm being fixed through one of its ends to a column that has a vertical support, being further that, the articulated arm is driven by a pneumatic/electro-pneumatic/hydraulic cylinder which has an end fixed to the base of said vertical support and an end opposite to the first one, fixed to said articulated arm.

BRIEF DESCRIPTION OF DRAWINGS

For greater clarity and understanding of the object of the present invention, it has been illustrated in several figures, in which the invention has been represented in one of the preferred embodiments, all by way of example, wherein.

DETAILED DESCRIPTION OF THE INVENTION

Making reference now to the figures, it is seen that the invention consists of a new spectrometric probe and an automatic sampler for sampling bulk material, where the probe allows to obtain information on parameters of interest of the composition of the material, such as protein, moisture, fat and others, directly in large quantities, avoiding the transfer of samples that shall be examined to external places under the observation and analysis of trained and specialized personnel, thus optimizing operation times and reducing related costs. It is emphasized that, when referring to the operation of "sampling", it should be understood as any type of sampling of optical sampling parameters, scanning or analysis related to the field of the art without this necessarily implying the taking and extraction of physical samples of the material. Likewise, the probe of the present invention can operate with wavelengths that vary between visible and NIR, the range being used according to the needs and requirements of each user.

Figure 1:
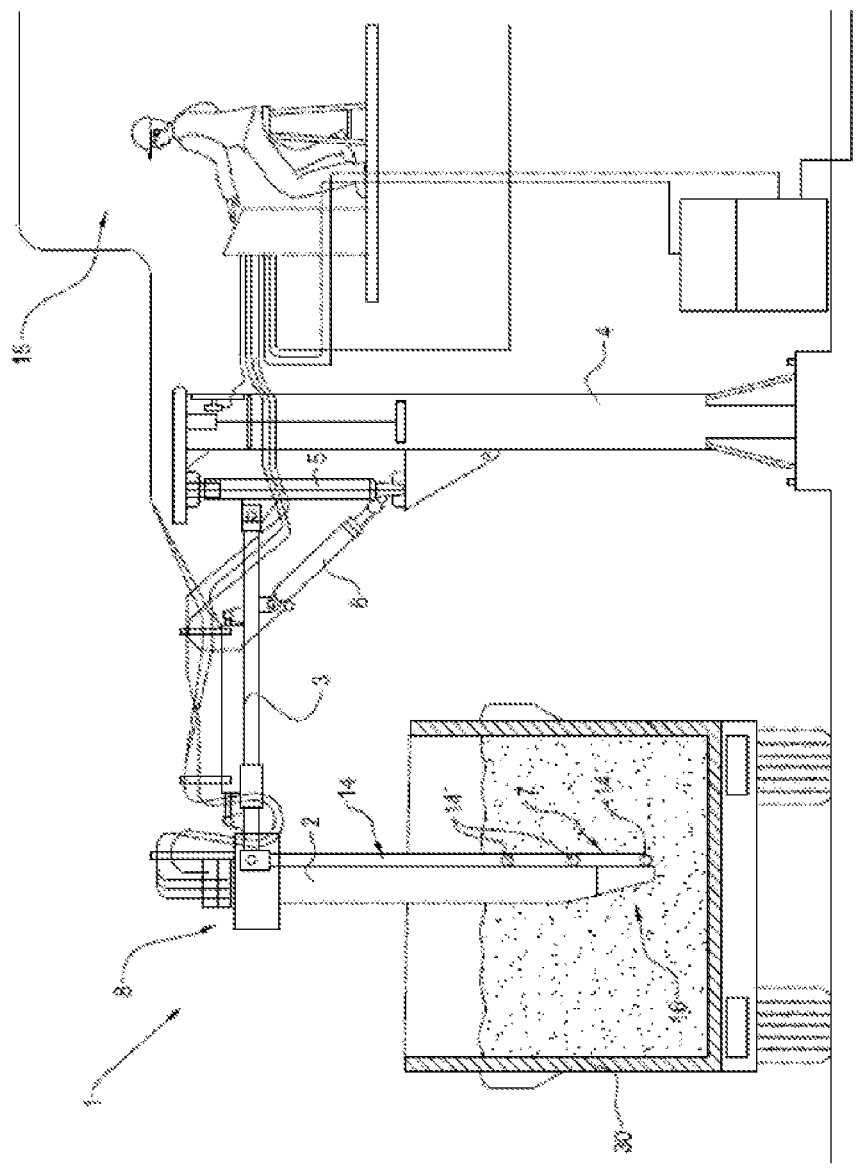
FIG. 1 shows an illustrative schematic view of an inspection plant for the sampling of bulk material, where an automatic sampler with a spectrometric probe according to the present invention can be observed, which is within a mass of bulk material contained in a trailer of a transport vehicle, such as a truck box or rail wagon.
Figure 2:
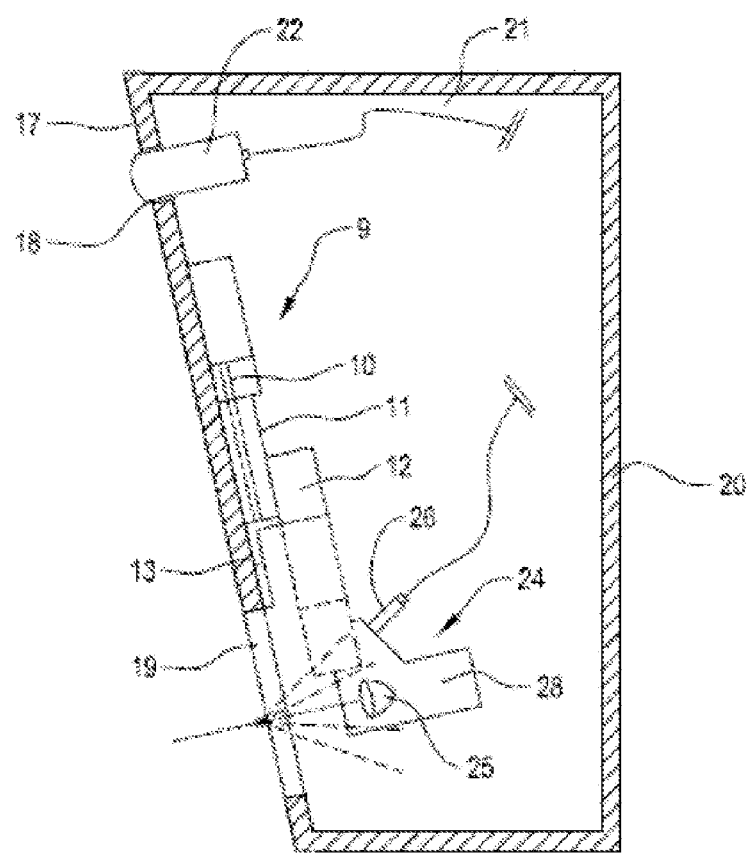
FIG. 2 shows a sectional side view of a sampling module according to the present invention.
Figure 3:
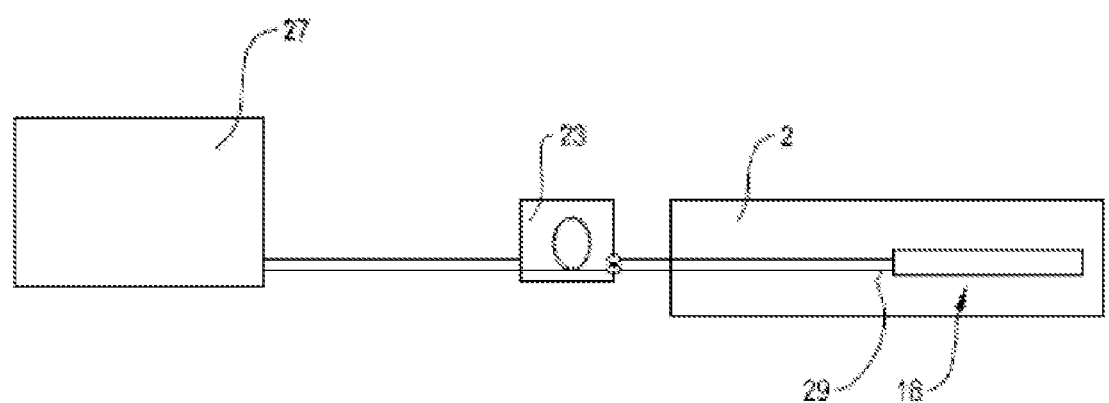
FIG. 3 shows a diagram of connection between the parts of the present invention.

Thus, and according to FIGS. 1 to 3, the automatic sampler of the present invention is indicated by the general reference (1) and comprises a tubular arm that may or may not be a spectrometric probe (2) according to the present invention, which is driven by an articulated arm (3) which is fixed through one of its ends to a column (4) that has a vertical support (5). The articulated arm (3) can be driven by a pneumatic/electro-pneumatic/hydraulic cylinder (6) which has an end fixed to the base of said support (5) and an end opposite to the first one, fixed to said articulated arm (3), thus allowing the free movement of the probe (2) in any direction and way. In turn, the probe (2) has a lower end (7) and an upper end (8).

According to one embodiment of the invention, the probe (2) has a spectrometric sampling module (16), which shall be referred to below.

According to another embodiment of the invention, the probe (2) and the sampling unit (16) are combined in what is known as an automatic sampling sampler and which includes a section (14) with a plurality of conduits (not shown) having each one, a respective nozzle for taking samples of grains (14'). It should be noted that the sampling nozzles (14') may be arranged in an upper, intermediate and lower section of the probe (2) and that they are well known in the field of the art and that for such reasons, we will not go into descriptive details about them.

On the other hand, in order to carry out the "opening" of the nozzles or intakes (14'), the probe can internally be provided with a rotating "C"-shaped half-shaft that is driven by an external motor (not shown). In this way, when opening the nozzles (14'), by turning the "C"-shaped half-shaft, the grains or bulk material enter allowing the taking of samples from the trailer of the truck or wagon for further analysis. The samples are transferred to an outbuilding or outer room (15) in which there is at least a trained and specialized personnel that performs the visual inspection of the samples and, if necessary, carries out the composition analysis as performed in conventional practice.

It is explained that both embodiments of the invention, i.e. the embodiment of the probe (2) with the spectrometric sampling module (16), and the embodiment of the sampler, with the section (14) which takes physical samples of grains, are both illustrated in FIG. 1 by a matter of reducing the number of drawings but it is clear that the probe (2) and the unit (16) can dispense with the section of tubes (14), (14').

In accordance with the present invention, the spectrometric probe is provided with the sampling module (16) which prevents the transfer of the grain samples to the outer room for carrying out the subsequent composition analysis thereof. That is to say, by means of the sampling module (16) according to the present invention, the obtaining of the different composition parameters of the grains can be carried out directly, significantly reducing times and related costs.

It is then that, the sampling module (16) can be fitted or mounted in the vicinity of the lower end (7) of the probe (2) and comprises a casing having a front wall (17) provided with a hole (18) and a transparent inspection window (19) that can be of quartz, sapphire or any other optical material that may be highly NIR (near infrared radiation) transmitter, a rear wall (20) and both side walls (21). Wherein, said sampling module (16) may comprise a material selected from the group consisting of metallic, polymeric, ceramic materials or a combination thereof. Likewise, said sampling module (16) is internally provided with at least one capacitive sensor (22) that can be arranged outwards and just beyond the hole (18) made on the front wall (17) of the module (16), or else right above, to come into contact with the bulk material, and which is connected to an electronic control unit (23). Said sampling module also has at least one optical sampling sensor (24) comprising a light source (25) defining a light beam along a lighting path directed towards said window (19), and a reader of light (26) reflected on the grain mass, wherein said reader (26) is directed according to said reading path and is connected to a remote control panel (27) by optical fiber (29).

It is emphasized that said light source (25) is mounted on a support (28) and can be a lamp or any type of related light source that is arranged adjacent to said transparent inspection window (19) provided on the front wall (17), while, said light reader (26) is a fiber optic reader which is also mounted on said support (28), at an angle with respect to the horizontal position of the light source (25) of between about 35° to 45. In this way, the beam of light emitted by the source (25) falls on the sample, producing a reflection of the beam at angles varying approximately between 35° and 45° and which is perceived and read by the reader (26) which is angularly arranged between said angles. The data read by the reader (26), are then sent to the control panel (27) who shall determine, based on different comparisons and data takings (mathematical model called calibration), the different composition parameters of the grains or sample.

For its part, said control panel (27) can contain a NIR spectrometer, being that it can also be visible according to the wavelength used, protected and thermally stabilized. It is of the watertight type, protected and thermally stabilized, with industrial touch screen display, with integrated diode array, while said optical sampling sensor (24) is an optical sensor that covers the entire spectral bandwidth. Although the capacitive sensor (22) arranged at the opposite end to the transparent inspection window (19) has been illustrated, this is not a limitation for the invention, since said capacitive sensor can be arranged in the vicinity of the transparent window (19) without any inconvenience.

On the other hand, when the probe (2) is introduced into the grain, the capacitive sensor (22) is intended to send a signal informing that the sampling module (16) is already completely within the mass of the bulk material. Conversely, when the probe (2) is removed from the mass of bulk material, the capacitive sensor (22) shall detect that it is no longer in contact with the mass of material and this information shall be used by the software to, for example, interrupt the measurements and data collection.

In order for a software provided in the equipment to be able to parameterize the measurements and plot the corresponding curves in a system of axes, the sampling module (16) also has a linear actuator (9) comprising an actuator (10), for example a stepping motor that moves a piston (11) carrying at its end a black plate (12) and a white plate (13) intended to be positioned opposite the reading path of the fiber optic reader (26) to determine the limit points, of null reading, that is to say of null reflection by interposition of the black plate and of maximum reading, that is to say of maximum reflection by interposition of the white plate. Wherein, said black plate is made of a material selected from the group consisting of a matte black anodized aluminum laser cut and/or black eva rubber while said white plate is made of a material selected from the group consisting of a rectangular cut of Glaze Teflon material but it could also be ceramic or gold-plated metal plate 2 to 4 nm thick, Spectralon® brand from Labsphere, Inc.

Thus, before beginning the reading of reflection on the bulk material, the linear actuator is moved to extend the piston and place the black plate so that it stands in front of the reading path of the fiber optic reader. There the software then establishes the zero point or zero reading point. Then the actuator is moved to place the white plate in the reading path of the fiber optic reader which shall read the reflection of the light emitted by the lamp that shall be reflected on the white plate that is made of a highly reflective material (e.g., Labsphere's Spectralon® material, which is a fluoropolymer that has the highest diffuse reflectance of any known material or coating over the ultraviolet, visible, and near-infrared regions of the spectrum). The reading of the light reflected on the white plate shall be taken by the software of the equipment as the maximum reflection point. Then, between the points of zero reflection and maximum reflection as determined by the software, the curves of reflections measured on the grain shall be drawn. This software can perform the system central command, acquisition, measurement, data recording and automatic communication with a computer cloud or with the plant system of the place.

In relation to near infrared radiation NIR, measurement through the use of Near Infrared Radiation is based on the ability of certain molecules to absorb energy in established bands. It is then an energetic phenomenon intimately related to the own and distinctive kinetics of the different molecules. This energy absorbed by a sample of bulk material results in a spectral image in the entire range of wavelengths in which the detector of the spectrometer is sensitive, being preferable to work between 900 nm and 2500 nm but understanding that the invention is not limited to said range, since it could be used without any inconvenience for any wavelength that varies between 400 nm and 3000 nm, being able to be Visible and/or NIR according to the needs of each user, and having thus other spectrometric ranges for the different applications that could occur in the future. That is, the probe of the present invention can operate with wavelengths that vary between NIR or visible according to the needs of each user. This image is distinctive and unique, characteristic of the product analyzed. Thus, from the analysis of which bands (location of peaks) make up the spectrum, it is concluded what the sample contains. From the analysis of how much energy has been absorbed (peak intensity), the concentration of the different constituents is calculated. Wherein, each molecular group (Proteins, Fatty Acids, Fibers, Starch) has a certain absorption in specific bands, and behaves as "transparent" against non-homologous bands.

In relation to the mode of operation of the probe, first a truck, wagon or vehicle for transporting grain bulk material (30) enters the sampling street. The trained and specialized operator enters the Bill of Lading, activating the corresponding record in the corresponding Software. The Sampler operator starts the sampling operation. The probe (2) is introduced in the first location of the load of the truck. The capacitive sensor (22) detects when the mass of bulk material covers the quartz window (19). The spectral acquisition process is automatically triggered by a light beam generated by the source (25) and passing through the window (19). The system works like a "camera", obtaining complete spectra. This "scanning" process continues until the probe (2) reaches the bottom and the sampling nozzles (14) are opened.

The software detects the opening pulse and stops the spectral acquisition. It averages the spectra taken in descent and delivers a partial result by sections. This allows the option of immediate and accurate re-samplings, saving notable times by repetition of operations once the sampling is completed. When starting the ascent, the pulse is detected by the Software restarting the spectral acquisition and continuing with the accumulation of complete punctual spectra. When the capacitive sensor (22) is left to the "air" (free of bulk material), the indication of finishing the sampling arrives at the software. It averages and delivers a partial result of samplings.

The process is repeated in each sampling. When finished, it is ordered to stop generating the total average of the truck, thus generating a complete grid for the cloud and system. The system is ready for the next truck/wagon that is triggered automatically with the first entry of the probe therein.

Thus, by means of the invention, partial quality determinations are achieved by probe lowering and by sampling (detection of specific foci and/or sampling repetition) without loss of time: precision of loads and fraud control.

Average final determinations by truck (end of truck) or wagon. Complete quality map by sampling and section (upper, middle and lower). Automatic information association with the origin of the truck/wagon: traceability. Visualization of average partial and final data (moisture, protein, fat) in real time in industrial tactile panel. Classification of raw materials for the improvement of the quality of processed products.

In turn, it is known that without data, historical records and real statistics, there is no way to improve the industry. The value of information is crucial to make correct decisions with the aim of enhancing and optimizing: production, quality, infrastructure, positioning in the market, adding value to the productive chain, efficient use of both soil and water resources, costs and benefits, intelligent and sustainable agriculture, control and traceability, care for the environment, among many others.

The sampling module that may or may not be fitted into the sampling probe, has been designed with the main objective of expanding and closing the grain quality control circle, generating reliable, traceable and historical information in pursuit of common welfare, managing to promote the sustainable development of regional agricultural production, improving and optimizing the nutritional composition of raw materials, with the efficient use of resources and through corrective actions.

On the other hand, it should be clear that although in the present description reference is made in an exemplary manner to the sampling of grains, this does not imply that the present invention is limited thereto, but that the sampling can be carried out in different types of bulk materials, either independently or jointly with other devices, provisions or related means without any inconvenience.

The invention claimed is:

1. A spectrometric probe for sampling bulk material, wherein the spectrometric probe comprises:
    at least one sampling module mounted on a section of the probe and which is formed by a casing having at least one front wall having a transparent inspection window,
    a capacitive sensor that is in the casing and protrudes outside the casing for contacting the mass of the bulk material to be sampled,
    at least one optical sampling sensor within said casing and directed according to a reading path towards said inspection window, the optical sampling sensor being operatively connected to a remote control panel,
    wherein said optical sampling sensor comprises a light source that defines a light beam along a path of illumination directed towards said window, and a reader of light reflected on the mass of the bulk material, wherein said reader is a fiber optic reader directed according to said reading path, said reader being connected to said control panel by optical fiber, and
    wherein the sampling module has a linear actuator comprising an actuator connected to a piston that carries at its end a black plate and a white plate that lie between temporary operative positions in front of the reading path of the fiber optic reader.

2. A spectrometric probe according to claim 1, wherein said light source and said fiber optic reader are mounted on a support and are arranged angularly offset between approximately 35° to 45°.

3. A spectrometric probe according to claim 1, wherein said control panel is a spectrometer, while said optical sensor is an optical sensor that covers all the spectrometric bands.

4. A spectrometric probe according to claim 1, wherein said capacitive sensor is operatively connected to an electronic control unit.

5. A spectrometric probe according to claim 1, wherein said sampling module comprises said front wall, a rear wall and respective side walls made of a material selected from the group consisting of metallic, polymeric, ceramic materials and a combination thereof.

6. A spectrometric probe according to claim 1, wherein said black plate is made of a material selected from the group consisting of a matte black anodized aluminum laser cut and/or black EVA rubber while said white plate is made of a material selected from the group consisting of a rectangular cut of a diffuse reflectance material from 2 to 4 nm thick.

7. An automatic sampler for sampling bulk material using the spectrometric probe according to claim 1, wherein the automatic sampler comprises:
    said probe that is driven by an articulated arm,
    a plurality of nozzles located in at least one upper, intermediate and lower section of the probe for taking samples of material,
    wherein the articulated arm fixed through one of its ends to a column that has a vertical support, and
    wherein the articulated arm is driven by a cylinder selected from the group consisting of a pneumatic cylinder, an electro-pneumatic cylinder, and a hydraulic cylinder with the cylinder having an end fixed to the base of said vertical support and an opposite end, fixed to said articulated arm.

* * * * *